United States Patent
Garcia et al.

(10) Patent No.: US 9,713,455 B2
(45) Date of Patent: Jul. 25, 2017

(54) WIRELESS X-RAY SYSTEM

(71) Applicant: CMT MEDICAL TECHNOLOGIES LTD., Yoqneam Ilit (IL)

(72) Inventors: Beatriz Matesanz Garcia, Paris (FR); Ilan Sivan, Bat Shlomo (IL)

(73) Assignee: CMT MEDICAL TECHNOLOGIES LTD., Yoqneam (IL)

( * ) Notice: Subject to any disclaimer, the term of this patent is extended or adjusted under 35 U.S.C. 154(b) by 0 days.

(21) Appl. No.: 15/224,889

(22) Filed: Aug. 1, 2016

(65) Prior Publication Data

US 2016/0331342 A1 Nov. 17, 2016

Related U.S. Application Data

(63) Continuation of application No. 14/296,601, filed on Jun. 5, 2014, now Pat. No. 9,402,592.

(60) Provisional application No. 61/831,305, filed on Jun. 5, 2013.

(51) Int. Cl.
*G01N 23/04* (2006.01)
*A61B 6/00* (2006.01)
*A61B 6/02* (2006.01)

(52) U.S. Cl.
CPC .......... *A61B 6/563* (2013.01); *A61B 6/4208* (2013.01); *A61B 6/4283* (2013.01); *A61B 6/4494* (2013.01); *A61B 6/465* (2013.01); *A61B 6/5294* (2013.01); *A61B 6/541* (2013.01); *A61B 6/542* (2013.01); *A61B 6/566* (2013.01); *A61B 6/025* (2013.01); *A61B 6/5241* (2013.01)

(58) Field of Classification Search
CPC ......... A61B 6/461; A61B 6/563; A61B 6/541; A61B 6/4283; A61B 6/4494; A61B 6/465; A61B 6/5294; A61B 6/542; A61B 6/566; A61B 6/025; A61B 6/5241
USPC .................................................. 378/62, 98.8
See application file for complete search history.

(56) References Cited

U.S. PATENT DOCUMENTS

| | | | |
|---|---|---|---|
| 6,797,960 B1 * | 9/2004 | Spartiotis | G01N 23/04 250/370.01 |
| 8,243,883 B2 | 8/2012 | Omernick | |
| 2008/0099680 A1 * | 5/2008 | Bauer | G01T 7/00 250/336.1 |

(Continued)

*Primary Examiner* — Courtney Thomas
(74) *Attorney, Agent, or Firm* — Roach Brown McCarthy & Gruber, P.C.; Kevin D. McCarthy

(57) ABSTRACT

A system having an X-radiation generator; an X-radiation detector; and a portable computing device. The X-radiation detector has a first wireless communication module, and a non-volatile memory. The X-radiation detector is configured to: self-trigger acquisition of an X-radiation image, store the acquired X-radiation image, and transmit the X-radiation image (or a lower-resolution version) via the first wireless communication module. The portable computing device has a second wireless communication module, and a digital screen. The portable computing device is configured to receive the X-radiation image via the second wireless communication module that communicates with the first wireless communication module, display the X-radiation image on the digital screen, enable a user to select whether to discard the X-radiation image or to transmit the X-radiation image to a server, and responsive to the user selecting to transmit the X-radiation image to the server, transmit the X-radiation image to the server.

16 Claims, 6 Drawing Sheets

(56) References Cited

U.S. PATENT DOCUMENTS

| | | | |
|---|---|---|---|
| 2009/0046828 A1* | 2/2009 | Ohta | A61B 6/00 378/1 |
| 2010/0104066 A1 | 4/2010 | Foos | |
| 2011/0108732 A1 | 5/2011 | Watanabe | |
| 2012/0128127 A1* | 5/2012 | Chicchetti | G01T 7/00 378/62 |
| 2012/0189098 A1* | 7/2012 | Liu | A61B 6/4283 378/62 |

* cited by examiner

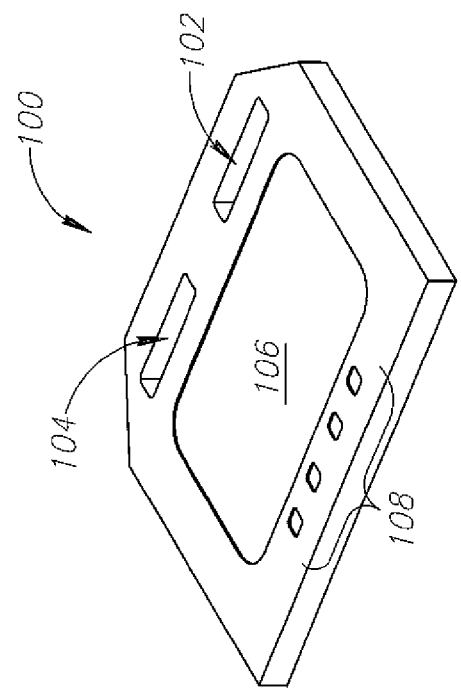
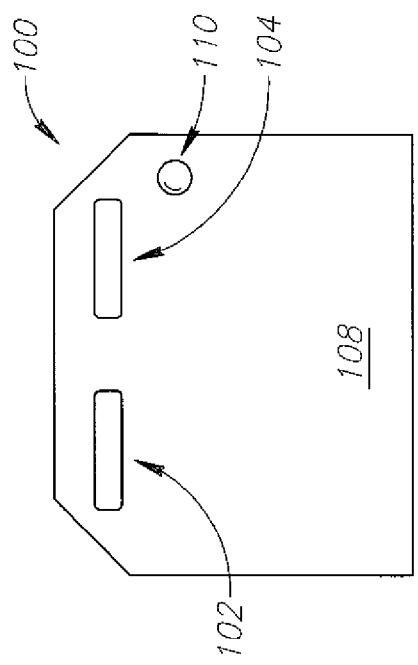
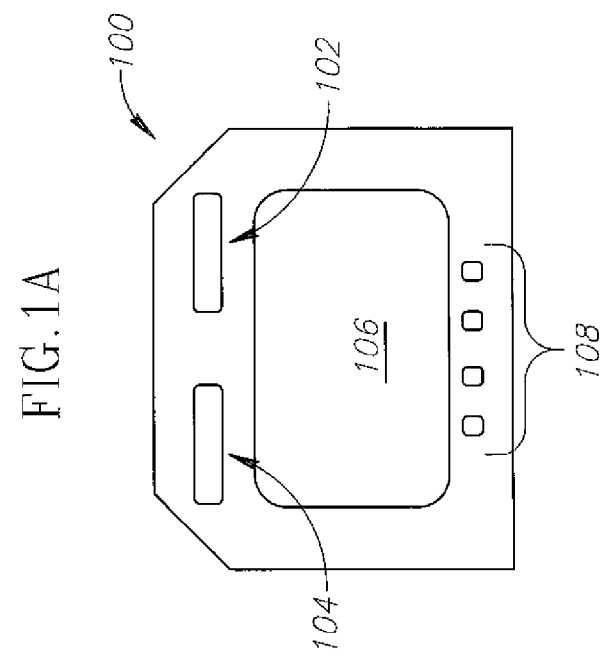

WIRELESS X-RAY SYSTEM

FIELD OF THE INVENTION

The invention relates to the field of X-ray systems.

BACKGROUND

X-ray imaging is widely used for examining an internal structure of a human body. X-ray images are, essentially, spatial distribution images of X-ray intensity passing through the body. Radiology has experienced significant advancements during the last decades. The advent of digital X-ray systems, which continue to replace older, film-based X-ray systems, has brought enhanced workflow and high image quality to medical imaging. In common medical imaging environments, digital X-ray imaging systems include an X-ray generator and one or more flat panel detectors (FPDs). The X-ray generator may be fixed or mobile and may use a detachable or a wireless detector. FPDs which feature self-triggering and automatic exposure control (AEC) have been recently introduced, allowing for more autonomous operation. Further recently, some vendors have rolled out radiology systems in which the operator's own portable device (such as a smart phone or a tablet computer) acts as the system's controller.

A digital image, whether of X-ray distribution or otherwise, is generally characterized by accurate and high-speed transmission of image information without damaging it. As typified by the technique of wireless local area networking, which has developed rapidly during recent years, image data acquired by an FPD can be transmitted to a computer system by wireless transmission, for purposes such as observation, storage, and management of the image data.

U.S. Pat. No. 8,243,883 to Arista et al. discloses a method for coordinating operation of X-ray detectors in a wireless X-ray system includes detecting multiple wireless X-ray detectors within an operative range of an X-ray base station, the detected X-ray detectors each having one of multiple possible statuses, including an active status corresponding to a designation of the X-ray detector as a desired recipient of radiation during a current X-ray imaging sequence, an inactive status corresponding to a designation of the X-ray detector as not the desired recipient of radiation during a current X-ray imaging sequence, and an unenabled status corresponding to the X-ray detector not being configured to operate with the X-ray base station. The method also includes determining the current status of each detected X-ray detector and displaying on a user-viewable screen a visual indication of the status of each detected X-ray detector.

U.S. Patent Application Publication No. US2011/108732 to Watanabe discloses a radiation detector to detect the radiation transmitted through an object while being in a portable state or mounted on a detector holder, a control unit to control capturing of a radiographic image using the radiation detector, and a plurality of relay stations to relay wireless communication from the radiation detector. The detector holder includes a detection unit to detect the mounting of the radiation detector. The control unit determines the usage pattern of the radiation detector or the mounting of the radiation detector on a detector holder based on detection information from the detection unit or a connection request from the radiation detector, and selects one of the relay stations based on the determination result.

U.S. Patent Application Publication No. US2010/104066 to Foos et al. discloses a mobile digital radiography system of a type including a mobile x-ray source; a mobile computer, the computer having a display for radiographic images and related information; a digital radiography detector, the detector and x-ray source in communication with and under control of the computer, means operatively associated with the computer for sending and receiving data concerning a patient, such data including diagnostic results, diagnostic images and requests for additional services, to and from separate image archiving and information systems; means operatively associated with the computer for comparing data from separate hospital image archiving and radiology information systems from a prior examination of a patient with data from a current examination of a patient using the mobile digital radiography system; and means operatively associated with the computer for aiding bedside interpretation of a patient's condition in view of the comparing of data from prior and current examinations.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a wireless radiation system comprising: a radiation generator comprising a first wireless communication module; and a radiation detector comprising a digital screen and a second wireless communication module, wherein said wireless radiation detector is configured to display a captured radiation image on said digital screen and to transmit the captured radiation image, using said second wireless communication module, to a server, wherein said first and second wireless communication modules are configured to wirelessly synchronize an radiation generation by said radiation generator and an exposure to the radiation by said radiation detector.

There is further provided, in accordance with an embodiment, a wireless radiation detector comprising: a radiation detection module; a wireless communication module; a digital screen; and a hardware processor configured to (a) operate said digital screen to display a radiation image captured by said radiation detection module, and (b) operate said wireless communication module to transmit the radiation image to a server.

In some embodiments, said wireless radiation detector is configured to display the captured radiation image in full quality.

In some embodiments, said wireless radiation detector is configured to display the captured radiation image in preview quality.

In some embodiments, said radiation detector further comprises a human interface device.

In some embodiments, said human interface device comprises said digital screen being a touch screen.

In some embodiments, said radiation detector is further configured to enable a user to determine whether to transmit the radiation image or to discard the radiation image.

In some embodiments, the radiation detector is further configured to provide a clean (calibrated) image.

In some embodiments, said radiation detector is further configured to post-process the radiation image.

In some embodiments, hardware processor is further configured to interface with a body parameter sensor, to synchronize radiation acquisition with the body parameter.

In some embodiments, said body parameter comprises breathing.

In some embodiments, said body parameter comprises body movement.

In some embodiments, said body parameter comprises a timing mechanism.

In some embodiments, said radiation comprises X-radiation.

In some embodiments, the wireless radiation detector further comprises a human interface device.

In some embodiments, said radiation detection module and said wireless communication module are mounted back-to-back.

There is further provided, in accordance with an embodiment, a method for radiation image acquisition, comprising: receiving X-radiation by a wireless radiation detector; translating the X-radiation to a digital image; and displaying the digital image on a digital screen integrally formed with the wireless radiation detector.

In some embodiments, the method further comprises providing a user interface configured to enable a user to determine whether to transmit the digital image or to discard the digital image.

In some embodiments, the method further comprises reading a printed patient identifier.

In some embodiments, the method further comprises converting the digital image to a DICOM file and automatically embedding the user identifier in the DICOM file.

In some embodiments, the method further comprises wirelessly transmitting the DICOM file to a DICOM server, using a wireless communication module integrally formed with the wireless radiation detector.

In some embodiments, said reading of the printed patient identified is performed using a barcode reader integrally formed with the wireless radiation detector There is further provided, in accordance with an embodiment, a distributed radiation system comprising: a radiation technician workstation comprising a non-volatile memory having stored thereon a software program for controlling multiple operations of an radiation room, said software program comprising an API (Application Program Interface); and one or more portable devices configured to wirelessly communicate with said workstation and to access said API, so as to control one or more of the multiple operations of the radiation room.

In some embodiments, said one or more portable computing devices comprise one or more tablet computers.

There is further provided, in accordance with an embodiment, a wireless radiation system comprising: a radiation generator; a radiation detector comprising a first wireless communication module and a non-volatile memory, wherein said radiation detector is configured to store a captured radiation image in said non-volatile memory; a portable device comprising a second wireless communication module and a digital screen; wherein said first and second wireless communication modules are configured to wirelessly interconnect so as to transfer the captured radiation image to said portable computing device for display on said digital screen.

In some embodiments, said one or more portable devices are selected from the group consisting of: a tablet computer and a smart phone.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 1A shows an exemplary radiation detector in a front view;

FIG. 1B shows the exemplary radiation detector in a rear view;

FIG. 1C shows the exemplary radiation detector in a perspective view;

DETAILED DESCRIPTION

Wireless Radiation Detector, System and Method

Figure 2:
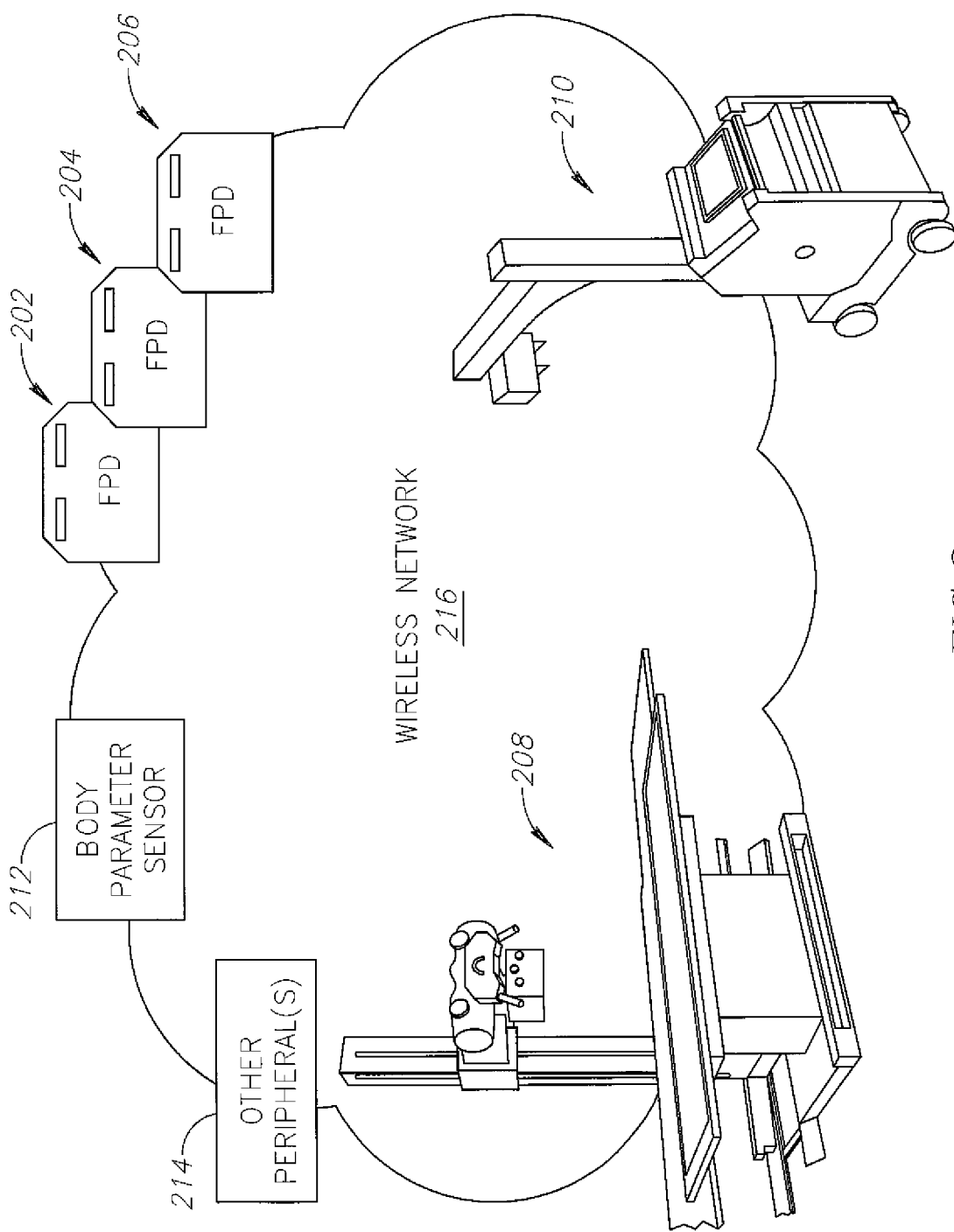
FIG. 2 shows a wireless radiation environment.

A wireless radiation detector, a wireless radiation system comprising the detector, and a method of using the same are disclosed herein. In some embodiments, the radiation is X-radiation. The radiation detector is optionally a flat panel detector (FPD), which is equipped, advantageously, with a digital screen embedded in its surface opposite the surface facing an radiation generator. The digital screen may enable medical personnel, such as a radiography technician, a physician and/or the like, to preview an acquired radiation image immediately following its acquisition, without the need to upload the image to a separate display device for viewing.

With radiation imaging constituting a significant diagnosis tool for physicians, specifically in urgent medicine environments, the importance of streamlining and expediting the radiation imaging procedure is great. It may be highly advantageous to shorten the time duration between radiation acquisition and diagnosis. The present wireless radiation detector, which features, in some embodiments thereof, the embedded digital screen, may be of great contribution to this end. Having such a screen, the technician can easily evaluate the quality of the resulting image. Further yet, the detector may have a preview quality or a full quality screen attached to it for displaying the resulting clinical image. Then, a radiologist or physician can diagnose the image without the need in expensive and cumbersome workstations.

The present wireless radiation system, advantageously, may be a highly-modular system made of multiple building blocks, which the user may combine or separate according to changing needs. The connection between at least some of the building blocks, if not all, is optionally wireless.

The connection between at least some of the building blocks may utilize a wireless enabler (also "wireless access point"). The wireless enabler may be a device packaged, for example, in a small box, and configured to form a bridge between normally-wired appliances of the radiation room and a wireless network of the radiation room. To this end, the wireless enabler may include a wired communication module, such as a serial or a parallel module, configured to directly connect to the radiation room appliance—for example a radiation generator, a breathing sensor, etc. The wireless enabler further includes a wireless communication module configured to wirelessly interface with a workstation at the radiation room. A hardware controller included in the enabler then bridges between the wired connection to the appliance and the wireless connection to the workstation, such that the appliance may be controller by the workstation wirelessly.

Among the building blocks of the system is an X-radiation generator having a wired or wireless communication module, for communicating with another building block, namely—a radiation detector which features a digital screen and is also equipped with a wired or wireless communication module. The two wired or wireless communication modules, that of the generator and that of the detector, may communicate with one another in order to wirelessly synchronize generation of X-radiation by the generator and exposure to the X-radiation by the detector. Alternatively or additionally, the detector may feature self-triggering and automatic exposure control (AEC), so that no wired or wireless synchronization between the generator and the detector is required.

Furthermore, the detector may utilize its wireless communication module for transmitting the captured radiation image to a server. The server may be a local workstation of the pertinent radiation room and/or a PACS (picture archiving and communication system) server. PACS is a medical imaging technology which provides economical storage of and convenient access to images from multiple modalities. PACS uses the DICOM (Digital Imaging and Communications in Medicine) format for storage and transfer of images. DICOM is a standard for handling, storing, printing, and transmitting information in medical imaging. See National Electrical Manufacturers Association, *The DICOM Standard*, available at http://medical.nema.org/standard.html.

Further building blocks of the system may be one or more sensors configured to sense different body parameters. As one example, it is often required to synchronize radiation acquisition with a specific stage in a patients breathing cycle. A breathing sensor may be used for this purpose. The breathing sensor may be wirelessly paired with the generator and/or the detector, to perform the synchronization.

Similarly, the system may be open to the addition of new peripheral devices. Each device which has a compatible wired or wireless networking module may be added to the system by being registered and authenticated by a host—either the work station, detector or the generator. Examples to such devices include digital video cameras which may be added to surgical systems for avoiding undesired exposure to the patient and to the personnel when positioning is not optimal. Encoders may be added to the tube arm and/or to the patient couch, thus allowing more sophisticated procedures such as stitching and tomosynthesis. One or more motion indicators may be added for trauma and/or for neonatal cases. The motion indicators may detect voluntary and/or involuntary body movement. Timers and blood monitors can be integrated into application of contrast-enhanced imaging. Further, a moving grid can be easily introduced into the system, with its indicator for proper motion synchronizing the radiation exposure. In general, room upgrades by adding new peripherals may be performed without the need for complex hardware and/or software updates.

Also disclosed herein is a radiography room which may be entirely wireless network-based. In some embodiments, functional room components have integrated communication modules (also "boards"), which allow inter-room and intra-room communication, as well as communication to one or more remote servers, such as DICOM servers of the pertinent medical facility. Thus, a single portable FPD may serve a plurality of radiation rooms.

The detector, which has wireless networking capabilities, may either function as a net "master", controlling the full room operation, and/or can act as a "slave", being operated by the operator's host, such as the operator's workstation located in the room or adjacent to the room.

The detector, in some embodiments, may be totally independent in operation. It may include internal triggering and AEC, and also internal, non-volatile memory for saving a large amount of acquired images. Further, it may be equipped with a barcode reader, an NFC device or any other electrical device for capturing the patient details, such as a patient ID. These details are then appended on a data file header, such as the DICOM file header, and may be displayed both on the preview image and on the full image. Optionally, the detector encompasses sufficient computer power for processing the preview and the full image and wrapping it in a DICOM format, then sending the images directly to the DICOM server over a network.

Another aspect of the invention lies in making the present wireless radiation system highly customizable. It allows the user to adjust the graphical look, system work flow, system language, image processing and display features, preparing a user-specific setup (templates) that can be saved and used by one or more users. The system thus adapts its characteristic to each registered user upon identification by password or by biometric means.

Another aspect of the invention is the use of the generic system for operation in different regions of the world (with immediate adjustments of work flow and languages), to different modalities (adding and extracting modality specific widgets) and to different OEMs (original equipment manufacturers).

Distributed X-Ray System

Further disclosed herein is a distributed radiation system, in which one or more capabilities of a workstation of a radiation technician are delegated to one or more portable computing devices, to be placed inside or outside an radiation room.

The delegation may be achieved by providing the workstation with a software program having an open API (Application Program Interface), the program stored on the workstation, which software program controls multiple operations of the radiation room, such as patient details registration, radiation image acquisition, radiation image manipulation, radiation image DICOM transmittal, etc. Advantageously, the API enables access by external devices, such as the one or more portable computing devices, to the various operations available in the workstation.

The workstation and the one or more portable computing devices may communicate wirelessly and/or over a wired network. The following are some examples of how one or more portable computing devices may be implemented and used in the distributed radiation system:

A portable computing device, such as a tablet computer, may be positioned on or in association with a stationary radiation generator 208 or a mobile radiation generator 210 (as in FIG. 2). This may enable the technician to set various acquisition parameters while standing next to the patient, or even to execute the acquisition itself while standing there, protected by a lead apron. Furthermore, the technician may use the tablet computer for reviewing the acquired image, or a lower-resolution version thereof, without having to first pull the panel from beneath the patient and connecting it to a workstation.

A portable or stationary device, such as a tablet computer, may be positioned at the entrance to the X-room, to register patient presence and details, for example by typing in, by swiping or waving a smart card, etc. The patient's registration details are then inserted directly into the technician's workstation, through the API.

A portable computing device, such as a tablet computer, may be hand-held by the technician and used for acquiring various personal details from the patient, setting various acquisition parameters while standing next to the patient, and/or executing the acquisition itself while standing there, protected by a lead apron. The device may be further used by the technician for retrieving past images of the same patient from a PACS (picture archiving and communication system), and comparing them, in real time, to images presently acquired.

A portable or stationary computing device, such as a tablet computer, may be hand-held by the technician or positioned on or in association with a stationary radiation generator 208 or a mobile radiation generator 210 (as in FIG. 2). This device may completely replace the work station, and enable the technician to perform the entire radiation process, including acquisition and transmittal to PACS—at the device itself.

Wireless Interconnection between an X-Ray Detector and a Portable Computing Device Further disclosed herein are a system and a method for wireless interconnection between a radiation detector and a portable computing device. A radiation detector, optionally of the FPD type, may include a wireless communication module (such as a WLAN module, a BlueTooth module, etc.), a hardware processor and a non-volatile memory. Once an radiation image is acquired by the detector, its processor may save the image to the non-volatile memory, and make it available to external devices through the wireless communication module. Then, a portable computing device, such as a tablet computer, a smart phone and/or the like may wirelessly connect to the detector and download the acquired image, or at least a lower-resolution version thereof.

This interconnection may allow a technician who works with a mobile radiation generator 210 (as in FIG. 2) to acquire radiation of multiple patients, to immediately review an radiation image after its acquisition. Accordingly, if the radiation image is found by the technician to be less than satisfactory, the technician can immediately acquire another image. This prevents a situation in which a technician carries out a lengthy round of patient radiation acquisitions with the mobile generator, and only at the end of which round, when the images are downloaded to a workstations, discovers that some of the images are faulty and need to be re-taken.

Furthermore, having the portable computing device may eliminate the need to remove the detector from beneath the patient to view the image.

Reference is now made to FIGS. 1A, 1B and 1C, which show an exemplary radiation detector 100 (hereinafter simply "detector") in front, back and perspective views, respectively.

Detector 100 is optionally a flat panel detector (FPD), namely—it is encompassed in a substantially flat and planar housing, commonly having a thickness of up to a few centimeters. Each of the width and length of detector 100 may be in the range of a few dozen centimeters, although measurements which exceed those are also intended herein. Detector 100 optionally includes, for reasons of convenience, one or more handles, such as two handles 102 and 104, for easy carrying and positioning.

Inside detector 100 there is embedded a radiation detection module (not shown), configured to receive radiation such as X-ray, transduce the radiation to an electrical signal and then digitize the signal to form a digital radiation image. There is further embedded inside detector 100 a digital screen 106, mounted back-to-back with the detection module, such that the detector is positioned, for acquisition, with its front surface 108 facing a radiation tube of the radiation generator. Digital screen 106 is optionally an LCD (liquid crystal display) screen, and further optionally be a touch screen, such as a capacitive touch screen, a resistive touch screen or the like. In this case, the touch screen may serve as a human interface device (HID), and display a suitable graphic user interface (GUI) with which the user may interact. Additionally or alternatively, a HID may be in the form of one or more buttons, one or more pointing devices and/or the like, which are external to digital screen 106. As an illustrative example only, 4 buttons 108 are shown in the figure, below digital screen 106.

To operate both the detection module and digital screen 106, detector 100 further includes a hardware controller (not shown) having at least one hardware processor and associated circuitry, such as a non-volatile memory, a random access memory (RAM) and/or the like.

Detector 100 may further be equipped with a wireless communication module in control by the controller and optionally as an integral part thereof. The wireless communication module may be a WLAN (IEEE 802.11) module, a Bluetooth module and/or the like.

Detector 100 may further be equipped with a patient ID reading module, to enable convenient input of a patient's identifying information into the detector. For example, the patient ID reading module may be a barcode reader (or other device) 110, configured to read for instance two-dimensional and/or three-dimensional barcodes which are printed on the patient's bracelet, bed, and/or medical documents.

Reference is now made to FIG. 2, which shows a network diagram of a wireless radiation system, to further demonstrate how multiple detectors, such as FPD detectors 202, 204 and 206, being of the same type as detector 100 (FIGS. 1A-C), may be used in a wireless radiation environment. The illustrated radiation environment may further include one or more radiation generators, such as a stationary generator 208 and a mobile generator 210.

All of the detectors 202-206, stationary generator 208 and mobile generator 210 may interconnect via a same wireless network 216, which may utilize one or more protocols such as WLAN (IEEE 802.11), Bluetooth PAN (Personal Area Network) and the like. To this end, stationary generator 208 and mobile generator 210 may each be equipped with a suitable wireless communication module.

Wireless network 216 may have further connected to it a body parameter sensor 212, for synchronizing radiation acquisition by one or more of detectors 202-206 with the body parameter. For example, body parameter sensor 212 may be a breath sensor configured to sense a breathing stage (inhalation and exhalation) of the patient and automatically acquire an radiation image in a desired timing.

One or more other peripheral(s) 214 may also be connected to wireless network 216 using suitable wireless communication modules. Peripherals(s) 214 may communicate with one or more of detectors 202-206, stationary generator 208 and mobile generator 210 over wireless network 216. Such peripherals can be OCDs (Operator Controlled devices) that may be placed inside the X-Ray room in close proximity to the patient and allow the operator to perform functions without the need to go to the workstation, which is time consuming in an X-Ray environment. The OCDs can be mounted, for instance, on the tubes and allow for example to control the exposure parameters going to the generator, show the acquired image, show patient name, etc.

Figure 3:
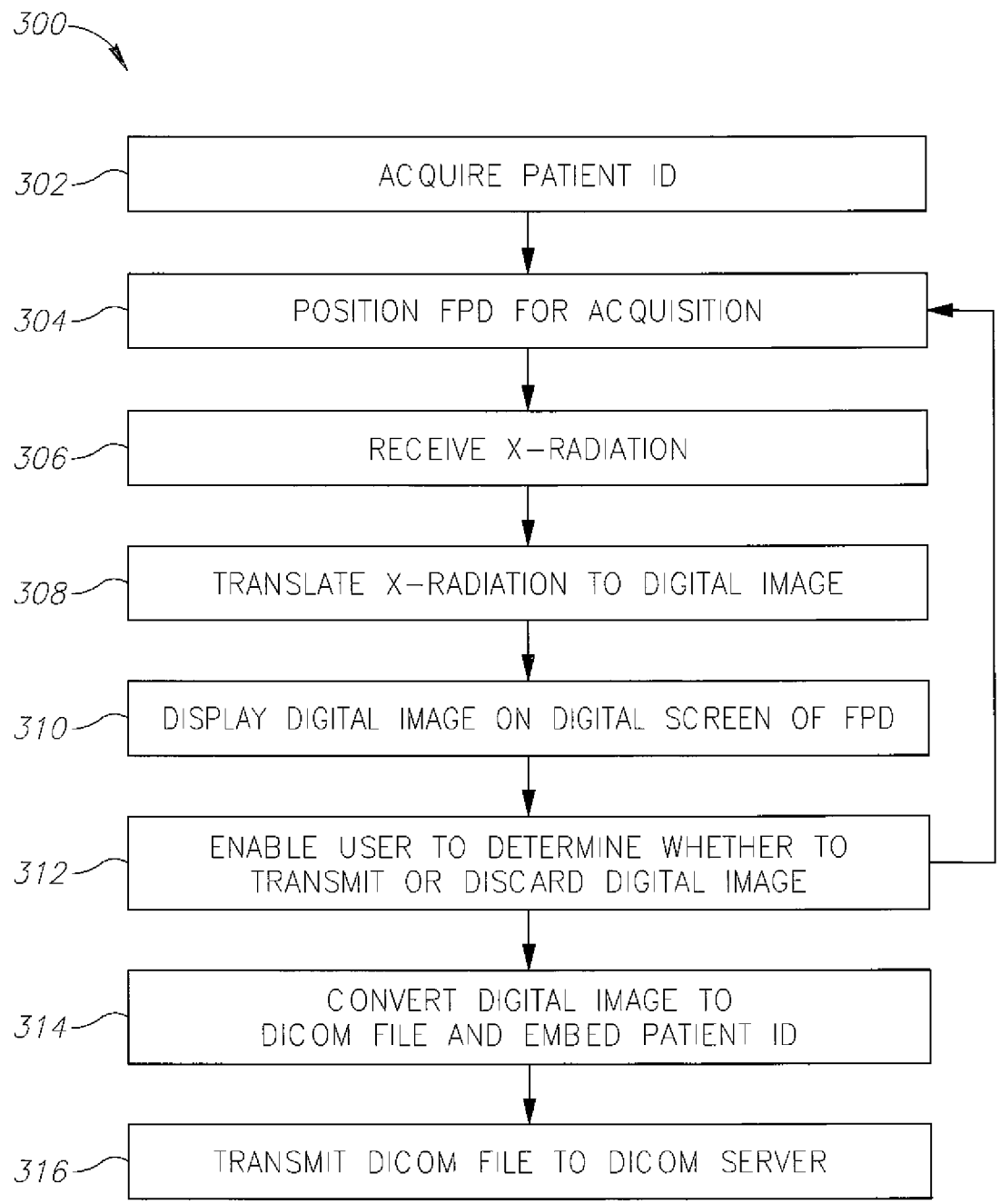
FIG. 3 shows a flowchart of a method for radiation acquisition.
Figure 4:
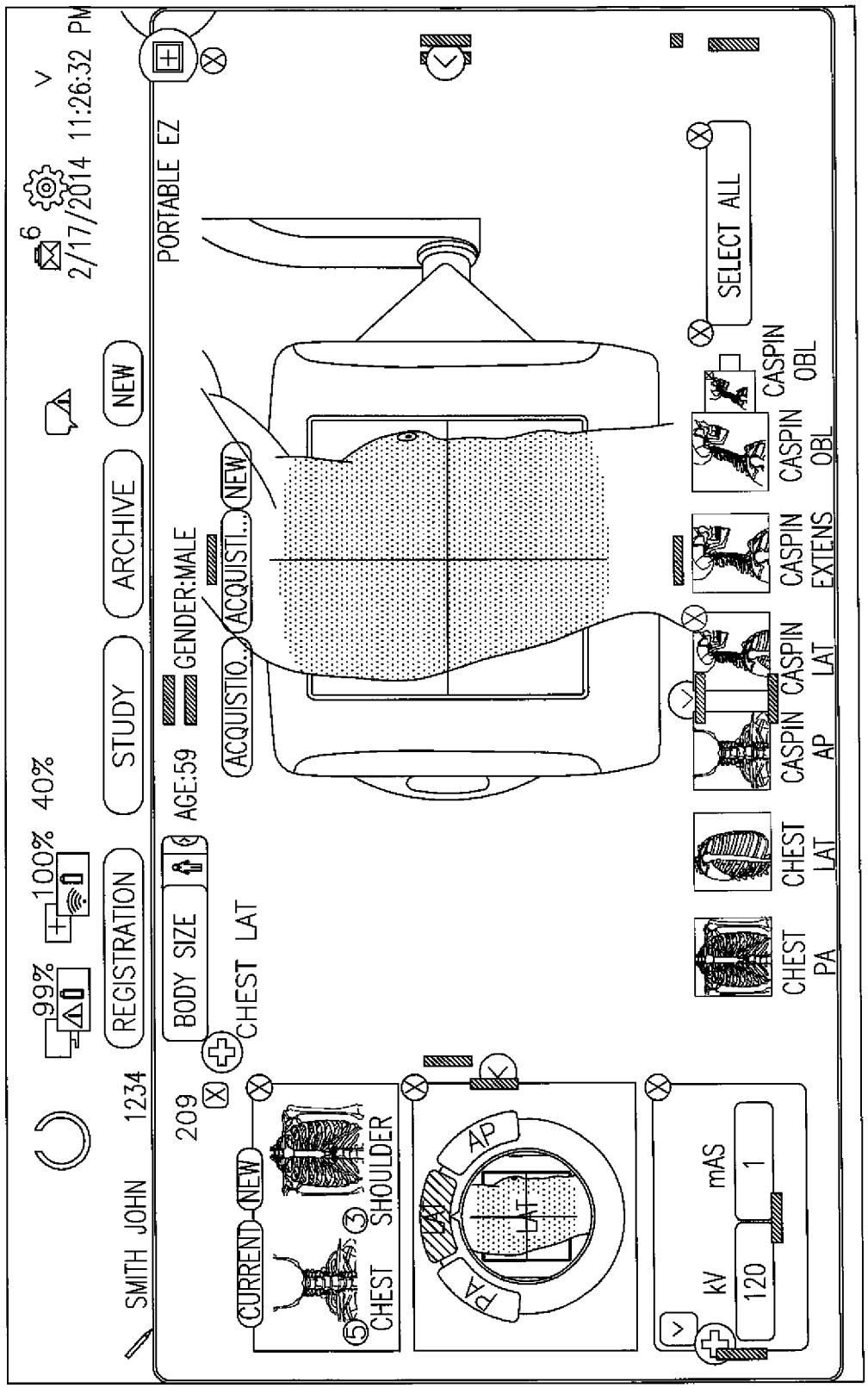
FIG. 4 shows an exemplary customizable graphical user interface (GUI) of a software application of the system.
Figure 5A:
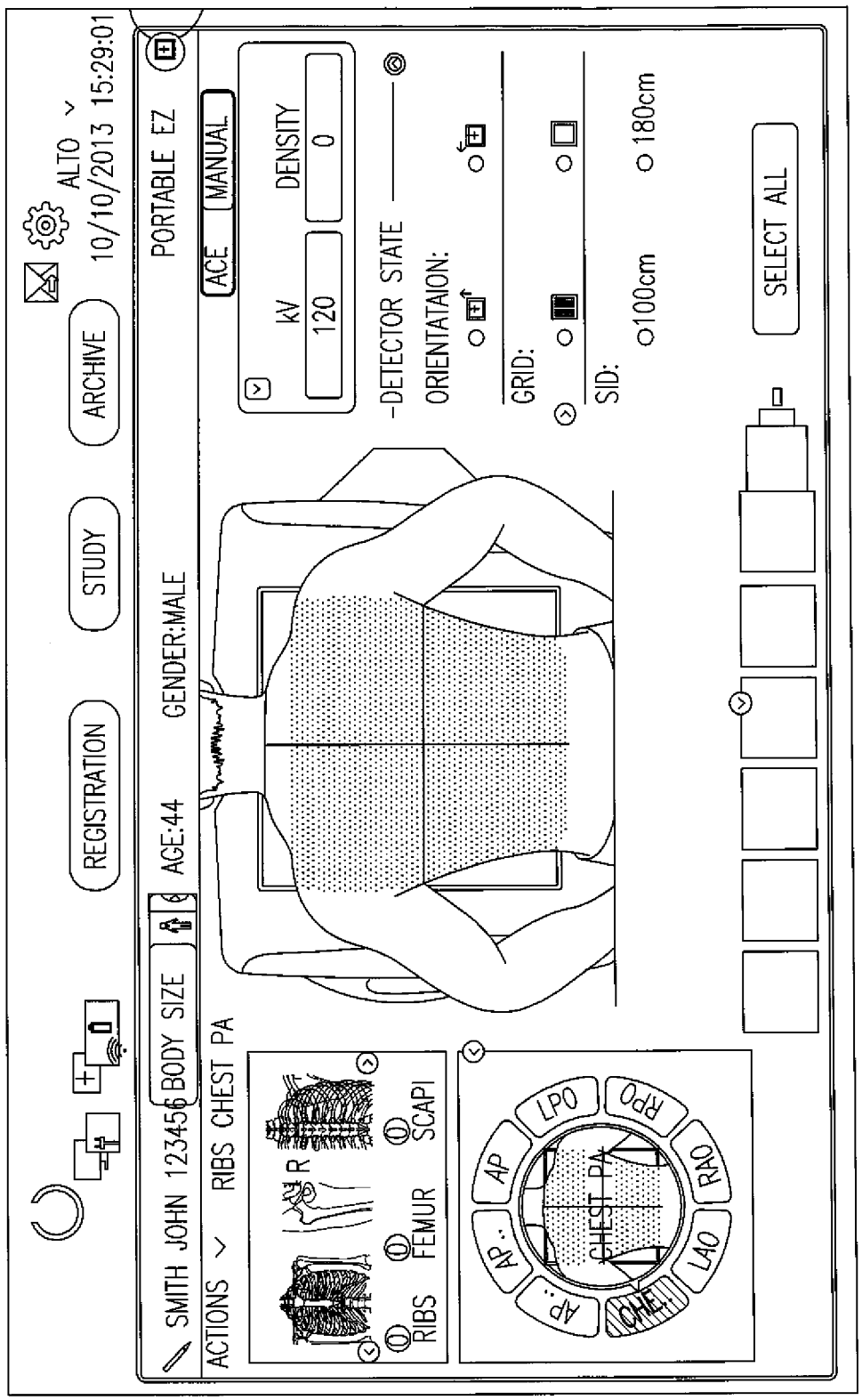
FIG. 5A shows an exemplary GUI of a software application of the system, depicting a controllable anti-scatter grid and source-to-imager distance (SID)
Figure 5B:
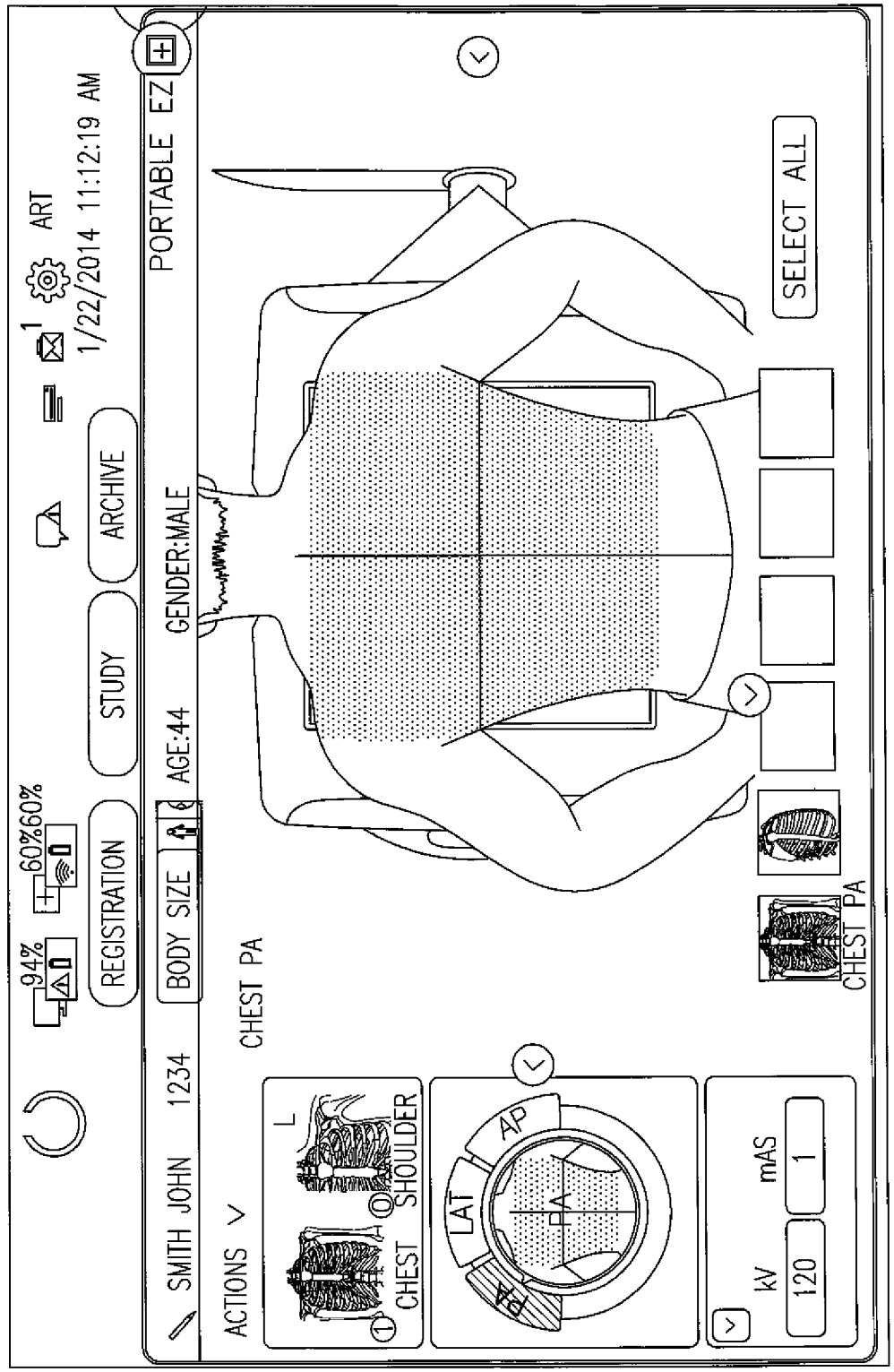
FIG. 5B shows an exemplary GUI of a software application of the system, without the controllable modules of FIG. 5A.

FIG. 3 shows a flow chart of an exemplary method 300 for radiation acquisition in the wireless radiation environment of FIG. 2.

In a step 302, an radiation technician (and/or another caregiver) may use an FPD, such as any one of detectors 202-206 of FIG. 2, for acquiring a patient ID, for example using a barcode reader integrally formed with the FPD. The patient ID may be a governmental ID number, a social security number, an ID designated to the patient by the medical facility, and/or the like. The patient ID may be imprinted on a label attached to a bracelet of the patient, to his or her bed and/or to his or her medical documents. The patient ID acquisition, despite being shown as the first step of method 300, may alternatively be performed at any other stage of the method.

In a step 304, the technician may position the FPD for acquiring a radiation image of the patient. The FPD may be positioned so as to receive radiation from a stationary or a mobile radiation generator, as may be the case, such as stationary generator 208 and mobile generator 210.

In a step 306, the FPD may receive the radiation from the generator, using either a self-triggering mechanism and/or automatic exposure control (AEC) of the FPD, or wireless synchronization between the FPD and the generator.

In a step 308, a hardware controller of the FPD may translate the received radiation to a digital image, and in a step 310, the hardware controller may display the digital image on a digital screen of the FPD.

In a step 312, the technician may review the digital image and decide whether the image is sufficient or whether a repeated acquisition is required. If a repeated acquisition is required, for example due to a blurred image, wrong positioning of the FPD, wrong positioning of the patient, motion of the patient and/or the like, the image may be discarded and the method may return to step 304. If the image is sufficient, the method may continue.

In a step 314, the digital image may be converted to a DICOM-format file or files, in which the patient ID acquired earlier may be automatically embedded, so that the technician does not have to input this information manually.

Finally, in a step 316, the DICOM file or files are transmitted, wirelessly, from the FPD to a remote DICOM server of the medical facility.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

What is claimed is:

1. A system comprising:
   (a) an X-radiation generator;
   (b) an X-radiation detector comprising:
      a first wireless communication module, and
      a non-volatile memory,
      wherein said X-radiation detector is configured to:
         (i) self-trigger acquisition of an X-radiation image upon detecting X-radiation generated by said X-radiation generator,
         (ii) store the acquired X-radiation image in said non-volatile memory,
         (iii) transmit a lower-resolution version of the X-radiation image via said first wireless communication module, and
         (iv) transmit the X-radiation image to a PACS (Picture Archiving and Communication System) server via said first wireless communication module; and
   (c) a portable computing device comprising:
      a second wireless communication module, and
      a digital screen,
      wherein said portable computing device is configured to:
         (v) receive the lower-resolution version of the X-radiation image via said second wireless communication module that communicates with said first wireless communication module,
         (vi) display the lower-resolution version of the X-radiation image on said digital screen,
         (vii) enable a user to select whether to discard the X-radiation image from said X-radiation detector or to transmit the X-radiation image from said X-radiation detector to said PACS server, and
         (viii) responsive to the user selecting to transmit the X-radiation image to the PACS server, cause said X-radiation detector to transmit the X-radiation image to the PACS server.

2. The system according to claim 1, wherein said portable computing device is further configured to wrap the X-radiation image in a DICOM (Digital Imaging and Communications in Medicine) format.

3. The system according to claim 1, wherein said X-radiation detector is an FPD (Flat Panel Detector).

4. The system according to claim 1, wherein said X-radiation detector is further configured for automatic exposure control (AEC).

5. The system according to claim 1, wherein:
   said X-radiation generator comprises a third wireless communication module; and
   said first and third wireless communication modules are configured to wirelessly synchronize radiation generation by said X-radiation generator and exposure to the radiation by said X-radiation detector.

6. The system according to claim 1, wherein:
   said X-radiation generator comprises a third wireless communication module;
   said portable computing device is further configured to enable the user to cause said X-radiation generator to generate X-radiation, by causing said second wireless communication module to communicate with said third second wireless communication module.

7. The system according to claim 1, wherein said portable computing device is further configured to:
   enable the user to set various X-radiation image acquisition parameters; and
   operate said second wireless communication module to transmit the parameters to said X-radiation detector via said first wireless communication module.

8. The system according to claim 1, comprising multiple ones of said X-radiation detector, wherein said portable computing device is configured to perform actions (v) through (viii) with respect to each of said multiple X-radiation detectors.

9. The system according to claim 1, further comprising a body parameter sensor for wirelessly synchronizing the acquisition of the X-radiation image with the body parameter.

10. The system according to claim 9, wherein the body parameter sensor is a breathing sensor configured to automatically cause the acquisition of the X-radiation image at a desired breathing stage of a patient.

11. A method comprising:
operating an X-radiation detector to:
self-trigger acquisition of an X-radiation image upon detecting X-radiation generated by an X-radiation generator,
store the acquired X-radiation image in a non-volatile memory of said X-radiation detector, and
transmit a lower-resolution version of the X-radiation image via a first wireless communication module of said X-radiation detector;
operating a portable computing device to:
receive the lower-resolution version of the X-radiation image via a second wireless communication module of said portable computing device that communicates with said first wireless communication module,
display the lower-resolution version of the X-radiation image on a digital screen of said portable computing device,
enable a user to select whether to discard the X-radiation image or to transmit the X-radiation image to a PACS (Picture Archiving and Communication System) server via said first wireless communication module; and
further operating said X-radiation detector to:
transmit the X-radiation image to the PACS server via said first wireless communication module, responsive to the user selecting to transmit the X-radiation image to the PACS server.

12. The method according to claim 11, further comprising operating said portable computing device to wrap the X-radiation image in a DICOM (Digital Imaging and Communications in Medicine) format.

13. The method according to claim 11, wherein said X-radiation detector is an FPD (Flat Panel Detector).

14. The method according to claim 11, wherein said X-radiation detector is configured for automatic exposure control (AEC).

15. The method according to claim 11, wherein:
said X-radiation generator comprises a third wireless communication module; and
the method further comprises at least one of:
operating said first and third wireless communication modules to wirelessly synchronize radiation generation by said X-radiation generator and exposure to the radiation by said X-radiation detector, and
enabling the user to cause said X-radiation generator to generate X-radiation, by causing said second wireless communication module to communicate with said third second wireless communication module.

16. The method according to claim 11, further comprising operating said portable computing device to:
enable the user to set various X-radiation image acquisition parameters; and
operate said second wireless communication module to transmit the parameters to said X-radiation detector via said first wireless communication module.

* * * * *